(12) United States Patent
Halas et al.

(10) Patent No.: US 8,045,152 B2
(45) Date of Patent: Oct. 25, 2011

(54) ALL OPTICAL NANOSCALE SENSOR

(75) Inventors: Nancy J. Halas, Houston, TX (US); Don H. Johnson, Houston, TX (US); Sandra Whaley Bishnoi, Wilmette, IL (US); Carly S. Levin, Houston, TX (US); Christopher John Rozell, Houston, TX (US); Bruce R. Johnson, Houston, TX (US)

(73) Assignee: William Marsh Rice University, Houston, TX (US)

( * ) Notice: Subject to any disclaimer, the term of this patent is extended or adjusted under 35 U.S.C. 154(b) by 1118 days.

(21) Appl. No.: 11/762,430

(22) Filed: Jun. 13, 2007

(65) Prior Publication Data

US 2008/0176212 A1    Jul. 24, 2008

Related U.S. Application Data

(60) Provisional application No. 60/804,793, filed on Jun. 14, 2006.

(51) Int. Cl.
*G01J 3/44* (2006.01)
(52) U.S. Cl. ........................................................ 356/301
(58) Field of Classification Search .................... 356/301
See application file for complete search history.

(56) References Cited

U.S. PATENT DOCUMENTS

| | | |
|---|---|---|
| 6,174,677 B1 | 1/2001 | Vo-Dinh |
| 6,219,137 B1 * | 4/2001 | Vo-Dinh ....................... 356/301 |
| 6,344,272 B1 | 2/2002 | Oldenburg et al. |
| 6,428,811 B1 | 8/2002 | West et al. |
| 6,645,517 B2 | 11/2003 | West et al. |
| 6,685,986 B2 | 2/2004 | Oldenburg et al. |
| 6,699,724 B1 | 3/2004 | West et al. |
| 6,778,316 B2 | 8/2004 | Halas et al. |
| 6,846,565 B2 | 1/2005 | Korgel et al. |
| 7,123,359 B2 | 10/2006 | Armstrong et al. |
| 7,144,622 B1 | 12/2006 | Stecher et al. |
| 7,147,687 B2 | 12/2006 | Mirkin et al. |

(Continued)

FOREIGN PATENT DOCUMENTS

WO    2005092286 A2    10/2005

(Continued)

OTHER PUBLICATIONS

Aden, Arthur L., et al., "Scattering of electromagnetic waves from two concentric spheres," Oct. 1951, pp. 1242-1246, vol. 22, No. 10, Journal of Applied Physics.

(Continued)

*Primary Examiner* — Kara E Geisel
(74) *Attorney, Agent, or Firm* — Conley Rose, P.C.; Rodney B. Carroll (57) ABSTRACT

A composition comprising a nanoparticle and at least one adsorbate associated with the nanoparticle, wherein the adsorbate displays at least one chemically responsive optical property. A method comprising associating an adsorbate with a nanoparticle, wherein the nanoparticle comprises a shell surrounding a core material with a lower conductivity than the shell material and the adsorbate displays at least one chemically responsive optical property, and engineering the nanoparticle to enhance the optical property of the adsorbate. A method comprising determining an optical response of an adsorbate associated with a nanoparticle as a function of a chemical parameter, and parameterizing the optical response to produce a one-dimensional representation of at least a portion of a spectral window of the optical response in a high dimensional vector space.

22 Claims, 3 Drawing Sheets

U.S. PATENT DOCUMENTS

| | | | |
|---|---|---|---|
| 7,371,457 | B2 | 5/2008 | Oldenburg et al. |
| 2003/0215638 | A1 | 11/2003 | Charnay et al. |
| 2004/0174520 | A1 | 9/2004 | Premasiri et al. |
| 2004/0229039 | A1 | 11/2004 | Wei et al. |
| 2005/0130324 | A1 | 6/2005 | West et al. |
| 2006/0050268 | A1* | 3/2006 | Talley et al. ............... 356/301 |
| 2007/0132043 | A1 | 6/2007 | Bradley et al. |
| 2008/0166706 | A1 | 7/2008 | Zhang et al. |
| 2008/0204742 | A1 | 8/2008 | Halas et al. |
| 2008/0241262 | A1 | 10/2008 | Lee et al. |
| 2009/0213369 | A1 | 8/2009 | Lee et al. |
| 2010/0009338 | A1* | 1/2010 | Zhang et al. ............... 435/5 |

FOREIGN PATENT DOCUMENTS

| | | |
|---|---|---|
| WO | 2006099494 A2 | 9/2006 |
| WO | 2006135393 A2 | 12/2006 |
| WO | 2006135393 A3 | 12/2006 |
| WO | 2008028130 A1 | 3/2008 |

OTHER PUBLICATIONS

Beversluis, Michael R., et al., "Continuum generation from single gold nanostructures through near-field mediated intraband transitions," Physical Review B, 2003, pp. 115433-1 to 115433-10, vol. 68, The American Physical Society.

Chen, Jingyi, et al., "Gold nanocages: bioconjugation and their potential use as optical imaging contrast agents," Nano Letters, 2005, pp. 473-477, vol. 5, No. 3, American Chemical Society.

Chen, Sihai, et al., "Monopod, bipod, tripod, and tetrapod gold nanocrystals," J. Am. Chem. Soc., 2003, pp. 16186-16187, vol. 125, No. 52, American Chemical Society.

Chumanov, George, et al., "Unusual extinction spectra of nanometer-sized silver particles arranged in two-dimensional arrays," J. Phys. Chem., 1996, pp. 5166-5168, vol. 100, No. 13, American Chemical Society.

Clark, Heather A., et al., "Optical nanosensors for chemical analysis inside single living cells. 1. Fabrication, characterization, and methods for intracellular delivery of PEBBLE sensors," Analytical Chemistry, Nov. 1, 1999, pp. 4831-4836, vol. 71, No. 21, American Chemical Society.

Clark, Heather A., et al., "Subcellular optochemical nanobiosensors: probes encapsulated by biologically localised embedding (PEBBLEs)," Sensors and Actuators B, 1998, pp. 12-16, vol. 51, Elsevier Science S. A.

Félidj, N., et al., "Optimized surface-enhanced raman scattering on gold nanoparticle arrays," Applied Physics Letters, May 5, 2003, pp. 3095-3097, vol. 82, No. 18, American Institute of Physics.

Foreign Communication from a related counterpart application—International Search Report and Written Opinion, PCT/US05/28967, May 4, 2007, 9 pages.

Gao, Ping, et al., "Surface-enhanced raman spectroscopy as a probe of adsorbate-surface bonding: benzene and monosubstituted benzenes adsorbed at gold electrodes," Office of Naval Research, Contract N00014-79-C-0670, Technical Report No. 51, Aug. 1985, 32 pages, Journal of Physical Chemistry.

Hallen, H. D., et al., "Raman spectroscopy: probing the border between near-field and far-field spectroscopy," SPIE Proceedings, 1998, 3 pages.

Härdle, Wolfgang, "Applied nonparametric regression," 1990, 2 pages, Cambridge University Press, USA.

Haslett, T. L., et al., "Can surface-enhanced raman scattering serve as a channel for strong optical pumping?" Journal of Chemical Physics, Jul. 22, 2000, pp. 1641-1646, vol. 113, No. 4, American Institute of Physics.

Haynes, Christy L., et al., "Plasmon-sampled surface-enhanced raman excitation spectroscopy," J. Phys. Chem. B, 2003, pp. 7426-7433, vol. 107, No. 30, American Chemical Society.

Hirsch, L. R., et al., "A rapid, whole blood immunoassay using metal nanoshells," 25th Annual International Conference of the IEEE EMBS, Cancun, Mexico, Sep. 17-21, 2003, pp. 3442-3443, IEEE.

Hirsch, L. R., et al., "A whole blood immunoassay using gold nanoshells," Analytical Chemistry, May 15, 2003, pp. 2377-2381, vol. 75, No. 10, American Chemical Society.

Hirsch, L. R., et al., "Nanoshell-mediated near-infrared thermal therapy of tumors under magnetic resonance guidance," PNAS, Nov. 11, 2003, pp. 13549-13554, vol. 100, No. 23, The National Academy of Sciences of the USA.

Huang, Xiaohua, et al., "Cancer cell imaging and photothermal therapy in the near-infrared region by using gold nanorods," J. Am. Chem. Soc., 2006, pp. 2115-2120, vol. 128, No. 6, American Chemical Society.

Jackson, J. B., et al., "Controlling the surface enhanced raman effect via the nanoshell geometry," Applied Physics Letters, Jan. 13, 2003, pp. 257-259, vol. 82, No. 2, American Institute of Physics.

Jackson, J. B., et al., "Surface-enhanced raman scattering on tunable plasmonic nanoparticle substrates," PNAS, Dec. 28, 2004, pp. 17930-17935, vol. 101, No. 52, the National Academy of Sciences of the USA.

Jeanmaire, David L., et al., "Surface raman spectroelectrochemistry. Part I. Heterocyclic, aromatic, and aliphatic amines adsorbed on the anodized silver electrode," J. Electroanal. Chem., 1977, pp. 1-20, vol. 84, Elsevier Sequouia S.A., Lausanne, The Netherlands.

Jin, Rongchao, et al., "Photoinduced conversion of silver nanospheres to nanoprisms," www.sciencemag.org, Nov. 30, 2001, pp. 1901-1903, vol. 294, Science.

Joo, Tai Ha, et al., "Surface-enhanced raman scattering (SERS) of 1-propanethiol in silver sol," 1986, pp. 5816-5819, vol. 90, No. 22, American Chemical Society.

Kerker, Milton, et al., "Surface enhanced raman scattering (SERS) by molecules adsorbed at spherical particles: errata," Applied Optics, Dec. 15, 1980, pp. 4159-4174, vol. 19, No. 24, Optical Society of America.

Kneipp, Katrin, et al., "Population pumping of excited vibrational states by spontaneous surface-enhanced raman scattering," Physical Review Letters, Apr. 1, 1996, pp. 2444-2447, vol. 76, No. 14, The American Physical Society.

Kneipp, Katrin, et al., "Single molecule detection using surface-enhanced raman scattering (SERS)" Physical Review Letters, Mar. 3, 1997, pp. 1667-1670, vol. 78, No. 9, The American Physical Society.

Kwon, Yong Joon, et al., "Vibrational spectroscopic investigation of benzoic acid adsorbed on silver," The Journal of Physical Chemistry, 1994, pp. 8481-8487, vol. 98, No. 34, American Chemical Society.

Lee, Sang Bok, et al., "Surface-enhanced raman scattering of o-mercaptobenzoic acid in silver sol," Journal of Raman Spectroscopy, 1991, pp. 811-817, vol. 22, John Wiley & Sons, Ltd.

Loo, Christopher, et al., "Gold nanoshell bioconjugates for molecular imaging in living cells," Optics Letters, May 1, 2005, pp. 1012-1014, vol. 30, No. 9, Optical Society of America.

Loo, Christopher, et al., "Immunotargeted nanoshells for integrated cancer imaging and therapy," 2005, pp. 709-711, vol. 5, No. 4, American Chemical Society.

Malynych, Serhiy, et al., "Poly(vinyl pyridine) as a universal surface modifier for immobilization of nanoparticles," J. Phys. Chem. B, 2002, pp. 1280-1285, vol. 106, No. 6, American Chemical Society.

Martell, Arthur E., et al., "Critical stability constants. vol. 1: amino acids," 1974, 2 pages, Plenum Press, New York.

Michota, A., et al., "Surface-enhanced raman scattering (SERS) of 4-mercaptobenzoic acid on silver and gold substrates," Journal of Raman Spectroscopy, 2003, pp. 21-25, vol. 34, John Wiley & Sons, Ltd.

Mie, G, "Contributions to the optics of turbid media, particularly of colloidial metal solutions," translation of "Annalen der Physik, 25, 3, 377-445 (1908)", Feb. 2, 1976, 73 pages, Royal Aircraft Establishment.

Mohri, Nobuyuki, et al., "Desorption of 4-aminobenzenethiol bound to a gold surface," Langmuir, 1998, pp. 2343-2347, vol. 14, No. 9, American Chemical Society.

Moskovits, M., et al., "The geometry of several molecular ions adsorbed on the surface of colloidal silver," The Journal of Physical Chemistry, 1984, pp. 1293-1298, vol. 88, No. 7, American Chemical Society.

Moskovits, Martin, "Surface-enhanced spectroscopy," Reviews of Modern Physics, Jul. 1985, pp. 783-826 plus 2 figures, vol. 57, No. 3, The American Physical Society.

Nordlander, P. et al., "Plasmon hybridization in nanoparticle dimers," Nano Letters, 2004, pp. 899-903, vol. 4, No. 5, American Chemical Society.

Oldenburg, S. J., et al., "Infrared extinction properties of gold nanoshells," Applied Physics Letters, Nov. 8, 1999, pp. 2897-2899, vol. 75, No. 19, American Institute of Physics.

Oldenburg, S. J., et al, "Light scattering from dipole and quadrupole nanoshell antennas," Applied Physics Letters, Aug. 23, 1999, pp. 1063-1065, vol. 75, No. 8, American Institute of Physics.

Oldenburg, S. J., et al., "Nanoengineering of optical resonances," Chemical Physics Letters, May 22, 1998, pp. 243-247, vol. 288, Elsevier Science B.V.

O'Neal, D. Patrick, et al., "Photo-thermal tumor ablation in mice using near infrared-absorbing nanoparticles," 2004, pp. 171-176, vol. 209, Elsevier Ltd.

Osawa, Masatoshi, et al., "Charge transfer resonance raman process in surface-enhanced raman scattering from p-aminothiophenol adsorbed on silver: Herzberg—Teller contribution," J. Phys. Chem., 1994, pp. 12702-12707, vol. 98, No. 48, American Chemical Society.

Patent application entitled "Nonconcentric nanoshells and methods of making and using same" by Nancy J. Halas, et al., filed Jun. 20, 2007, as U.S. Appl. No. 11/765,862.

Prodan, E., et al., "A hybridization model for the plasmon response of complex nanostructures," www.sciencemag. org, Oct. 17, 2003, pp. 419-422, Vol. 302, Science.

Radloff, C., et al., "Enhanced thermal stability of silica-encapsulated metal nanoshells," Applied Physics Letters, Jul. 30, 2001, pp. 674-676, vol. 79, No. 5, American Institute of Physics.

Rall, Jonathan, "Lidar for atmospheric trace gas detection," Geoscience and Remote Sensing Society Instrumentation and Future Technologies Committee (GRSS-IFT), http://www.ewh.ieee.org/soc/grss/ift/rall16.html, 2002, 5 pages, Geoscience and Remote Sensing Society.

Ramakrishna, R. S., et al., "Complexes of thallium(I) and thallium(III) with thiosalicylic acid (o-mercaptobenzoic acid) and salicylic acid," J. inorg. nucl. Chem.,1971, pp. 1940-1942, vol. 33, Pergamon Press, Great Britian.

Rechberger, W., et al., "Optical properties of two interacting gold nanoparticles," Optics Communications, 2003, pp. 137-141, vol. 220, Elsevier Science B.V.

Roweis, Sam T., et al., "Nonlinear dimensionality reduction by locally linear embedding," www.sciencemag.org, Dec. 22, 2000, pp. 2323-2326, vol. 290, Science.

Sherry, Leif J. et al., "Localized surface plasmon resonance spectroscopy of single silver nanocubes," Nano Letters, 2005, pp. A to E, American Chemical Society.

Smallbone, Kieran, et al., "The role of acidity in solid tumour growth and invasion," Journal of Theoretical Biology, 2005, pp. 476-484, vol. 235, Elsevier Ltd.

Su, K.-H., et al., "Interparticle coupling effects on plasmon resonances of nanogold particles," Nano Letters, 2003, pp. 1087-1090, vol. 3, No. 8, American Chemical Society.

Talley, Chad E., et al., "Intracellular pH sensors based on surface-enhanced raman scattering," Analytical Chemistry, Dec. 1, 2004, pp. 7064-7068, vol. 76, No. 23, American Chemical Society.

Talley, Chad E., et al., "Surface-enhanced raman scattering from individual au nanoparticles and nanoparticle dimer substrates," Nano Letters, 2005, pp. 1569-1574, vol. 5, No. 8, American Chemical Society.

Tenenbaum, Joshua B., et al., "A global geometric framework for nonlinear dimensionality reduction," ProQuest Science Journals, Dec. 22, 2000, pp. 2319-2322, vol. 290, Science.

Vaupel, Peter, et al., "Blood flow, oxygen and nutrient supply, and metabolic microenvironment of human tumors: a review," Harvard Medical School, Boston, Massachusetts, Dec. 1, 1989, pp. 6449-6465, vol. 49, Cancer Research.

Wells, Mona, et al., "Interactions between organized, surface-confined monolayers and vapor-phase probe molecules. 9. Structure/reactivity relationship betwen three surface-confined isomers of mercaptobenzoic acid and vapor-phase decylamine," Langmuir, 1996, pp. 1989-1996, vol. 12, No. 8, American Chemical Society.

Xu, Shuping, et al., "Surface-enhanced raman scattering studies on immunoassay," Journal of Biomedical Optics, May/Jun. 2005, pp. 031112-1 to 031112-12, vol. 10, No. 3, SPIE.

Yu, Yu-Ying, et al., "Gold nanorods: electrochemical synthesis and optical properties," The Journal of Physical Chemistry B, Aug. 21, 1997, pp. 6661-6664, vol. 101, No. 34, American Chemical Society.

Zhu, Zihua, et al., "Raman scattering enhancement contributed from individual gold nanoparticles and interparticle coupling," Nanotechnology, 2004, pp. 357-364, vol. 15, Institute of Physics Publishing Ltd., UK.

Aizpurua, J., et al., "Optical properties of gold nanorings," Physical Review Letters, Feb. 7, 2003, pp. 057401-1 to 057401-4, vol. 90, No. 5, The American Physical Society.

Brandl, Daniel W., et al., "Plasmon hybridization in nanoshell dimers," The Journal of Chemical Physics, 2005, pp. 024701-1 to 024701-11, vol. 123, American Institute of Physics.

Chen, Sihai, et al., "Synthesis and characterization of truncated triangular silver nanoplates," Nano Letters, 2002, pp. 1003-1007, vol. 2, No. 9, American Chemical Society.

Fredkin, D. R., et al., Resonant behavior of dielectric objects (electrostatic resonances), Physical Review Letters, Dec. 19, 2003, pp. 253902-1 to 253902-4 vol. 91, No. 25, The American Physical Society.

Futamata, M., et al., "Local electric field and scattering cross section of Ag nanoparticles under surface plasmon resonance by finite difference time domain method," J. Phys. Chem. B, 2003, pp. 7607-7617, vol. 107, American Chemical Society.

Grady, N. K., et al., "Influence of dielectric function properties on the optical response of plasmon resonant metallic nanoparticles," Chemical Physics Letters, 2004, pp. 167-171, vol. 399, Elsevier B.V.

Hao, Encai, et al., "Synthesis and optical properties of "branched" gold nanocrystals," Nano Letters, 2004, pp. 327-330, vol. 4, No. 2, American Chemical Society.

Jackson, J. B., et al., "Silver nanoshells: variations in morphologies and optical properties," J. Phys. Chem. B, 2001, pp. 2743-2746, vol. 105, No. 14, American Chemical Society.

Johnson, P. B., et al., "Optical constants of the noble metals," Dec. 15, 1972, pp. 4370-4379, vol. 6, No. 12, Physical Review B.

Link, Stephan, et al., "Spectral properties and relaxation dynamics of surface plasmon electronic oscillations in gold and silver nanodots and nanorods," J. Phys. Chem. B, 1999, pp. 8410-8426, vol. 103, No. 40, American Chemical Society.

Maier, Stefan A., et al., "Optical pulse propagation in metal nanoparticle chain waveguides," Physical Review B, 2003, pp. 205402-1 to 205402-5, vol. 67, The American Physical Society.

Marton, J. P., et al., "Optical properties of aggregated metal systems: interband transitions," Feb. 15, 1977, pp. 1719-1727, vol. 15, No. 4, Physical Review B.

Michalet, X., et al., Quantum dots for live cells, in vivo imaging, and diagnostics, Jan. 28, 2005, pp. 538-544, vol. 307, Science.

Moskovits, Martin, et al., "Engineering nanostructures for giant optical fields," Chemical Physics Letters, 2004, pp. 91-95, vol. 397, Elsevier B.V.

Nie, Shuming, et al., "Probing single molecules and single nanoparticles by surface-enhanced Raman scattering," Feb. 21, 1997, pp. 1102-1106, vol. 275, Science.

Oubre, C., et al., "Finite-difference time-domain studies of the optical properties of nanoshell dimers," J. Phys. Chem. B, 2005, pp. 10042-10051, vol. 109, No. 20, American Chemical Society.

Ouyang, Feng, et al., "Accurate modeling of particle-substrate coupling of surface plasmon excitation in eels," Ultramicroscopy, 1989, pp. 345-349, vol. 31, Elsevier Science Publishers B.V. (North-Holland).

Pastoriza-Santos, Isabel, et al., "Synthesis of silver nanoprisms in DMF," Nano Letters, 2002, pp. 903-905, vol. 2, No. 8, American Chemical Society.

Prodan, E., et al., "Plasmon hybridization in spherical nanoparticles," Journal of Chemical Physics, Mar. 15, 2004, pp. 5444-5454, vol. 120, No. 11, American Institute of Physics.

Schuck, P. J., et al., "Improving the mismatch between light and nanoscale objects with gold bowtie nanoantennas," Physical Review Letters, Jan. 14, 2005, pp. 017402-1 to 017402-4, vol. 94, The American Physical Society.

Sershen, S. R., et al., "Temperature-sensitive polymer-nanoshell composites for photothermally modulated drug delivery," May 2000, pp. 293-298, John Wiley & Sons, Inc.

Shvets, Gennady, et al., "Engineering the electromagnetic properties of periodic nanostructures using electrostatic resonances," Physical Review Letters, Dec. 10, 2004, pp. 243902-1 to 243902-4, vol. 93, The American Physical Society.

Sun, Yugang, et al., "Shape-controlled synthesis of gold and silver nanoparticles," Dec. 13, 2002, pp. 2176-2179, vol. 298, Science.

Tam, Felicia, et al., "Geometrical parameters controlling sensitivity of nanoshell plasmon resonances to changes in dielectric environment," J. Phys. Chem. B, 2004, pp. 17290-17294, vol. 108, American Chemical Society.

Varsányi, György, et al., "Assignments for vibrational spectra of seven hundred benzene derivatives," 1974, 1 page, Wiley, New York.

Westcott, S. L., et al., "Relative contributions to the plasmon line shape of metal nanoshells," Physical Review B, 2002, pp. 155431-1 to 155431-5, vol. 66, The American Physical Society.

Xu, Hongxing, et al., "Spectroscopy of single hemoglobin molecules by surface enhanced Raman scattering," Physical Review Letters, Nov. 22, 1999, pp. 4357-4360, vol. 83, No. 21, The American Physical Society.

Xu, Hongxing, et al., "Polarization-dependent surface-enhanced Raman spectroscopy of isolated silver nanoaggregates," ChemPhysChem, 2003, pp. 1001-1005, vol. 4, Wiley-VCH Verlag GmbH & Co. KGaA, Weinheim.

Burges, Christopher J. C., "Geometric methods for feature extraction and dimensional reduction," Chapter 1, The Data Mining and Knowledge Discovery Handbook, 2005, pp. 1-34 plus 1 cover page and 1 publishing page, Springer Science+Business Media, Inc., New York, New York, USA.

Chance, R. R., et al., "Molecular fluorescence and energy transfer near interfaces," Advances in Chemical Physics, vol. XXXVII, 1978, pp. 1-65 plus 1 cover page, 1 publishing page, and 1 contents page, John Wiley & Sons, Inc., New York, USA.

Murphy, Catherine J., et al., "Surfactant-directed synthesis and optical properties of one-dimensional plasmonic metallic nanostructures," www.mrs.org/publications/bulletin, May 2005, pp. 349-355, vol. 30, MRS Bulletin.

Oubre, Chris, et al., "Optical properties of metallodielectric nanostructures calculated using the finite difference time domain method," J. Phys. Chem. B, 2004, pp. 17740-17747, vol. 108, No. 46, American Chemical Society.

Sullivan, Dennis M., "Electromagnetic simulation using the FDTD method," 2000, 4 pages, Institute of Electrical and Electronics Engineers, Inc., New York, New York, USA.

Taflove, Allen, et al., "Computational electrodynamics: the finite-difference time-domain method," Second Edition, 2000, 3 pages, Artech House, Inc. Boston, Massachusetts, USA.

"Experimental setup (Raman + STM)," http://w3,rz-berlin.mpg.de/pc/shg/shg_sers/Tip_enhanced/page3.html, 2004, 2 pages, Fritz-Haber-Institut der Max-Planck-Gesellschaft.

Pettinger, Bruno, et al., "A fine needle boosts light scattering," TERS highlights, http://w3.rz-berlin.mpt.de/pc/shg/shg_sers/Tip_enhanced/page1b_Highlight.html, 2004, 2 pages, Fritz-Haber-Institut der Max-Planck-Gesellschaft.

"SEM images of the tip," http://w3.rz-berlin.mpg.de/pc/shg/shg_sers/Tip_enhanced/page2.html, 2004, 2 pages, Fritz-Haber-Institut der Max-Planck-Gesellschaft.

"Surface enhanced Raman spectroscopy (SERS)," SERS mechanisms, http://w3.rz-berlin.mpg.de/pc/shg/shg_sers/ Tip_enhanced/page2.html, 2004, 7 pages, Frirz-Haber-Institut der Max-Planck-Gesellischaft.

"TERS introduction," http://w3.rz-berlin.mpg.de/pc/shg_sers/Tip_enhanced/page1.html, 2004, 2 pages, Fritz-Haber-Institut der Max-Planck-Gesellschaft.

"TERS results/Raman spectra," http://w3.rx-berlin.mpg.de/pc/shg/shg_sers/Tip_enhanced/page4.html, 2004, 2 pages, Fritz-Haber-Institut der Max-Planck-Gesellschaft.

Walker, Christopher, et al., "SERS—surface enhanced Raman scattering," Surface Science Techniques, http://www.uksaf.org/tech/sers.html, 1998, 2 pages, UK Surface Analysis Forum.

Wegner, Matthias, "SPR—surface plasmon resonance," Surface Science Techniques, http://www.uksaf.org/tech/spr.html, Mar. 9, 2009, 2 pages.

Office Action dated Aug. 25, 2008 (9 pages), U.S. Appl. No. 11/573,365, filed Aug. 20, 2007.

Office Action (Final) dated Apr. 8, 2009 (26 pages), U.S. Appl. No. 11/573,365, filed Aug. 20, 2007.

Office Action dated Jul. 9, 2010 (32 pages), U.S. Appl. No. 11/765,862, filed Jun. 20, 2007.

Office Action (Final) dated Mar. 21, 2011 (22 pages), U.S. Appl. No. 15/439,251, filed Jul. 16, 2009.

Prodan, E., et al., "Effects of dielectric screening on the optical properties of metallic nanoshells," Chemical Physics Letters, 2003, pp. 94-101, vol. 368, Elsevier Science B.V.

Prodan, E., et al., "Structural tunability of the plasmon resonances in metallic nanoshells," Nano Letters, 2003, pp. 543-547, vol. 3, No. 4, American Chemical Society.

Prodan, E., et al., "The effect of a dielectric core and embedding medium on the polarizability of metallic nanoshells," Chemical Physics Letters, 2002, pp. 325-332, vol. 360, Elsevier Science B.V.

Rodriguez, Kenneth R., et al., "Enhanced infrared absorption spectra of self-assembled alkanethiol monolayers using the extraordinary infrared transmission of metallic arrays of subwavelength apertures," Journal of Chemical Physics, Nov. 8, 2004, pp. 8671-8675, vol. 121, No. 18, American Institute of Physics.

Röseler, Arnulf, et al., "Infrared-optical characterization of metallic island films," Applied Spectroscopy, 1997, pp. 902-904, vol. 51, No. 6, Society for Applied Spectroscopy.

Sato, Shinri, et al., "Study of surface-enhanced IR absorption spectroscopy over evaporated Au films in an ultrahigh vacuum system," Applied Spectroscopy, 1997, pp. 1170-1175, vol. 51, No. 8, Society for Applied Spectroscopy.

Schneider, Grégory, et al., "Distance-dependent fluorescence quenching on gold nanoparticles ensheathed with layer-by-layer assembled polyelectrolytes," Nano Letters, 2006, pp. 530-536, vol. 6, No. 3, American Chemical Society.

Schrader, Bernhard, Editor, "Infrared and raman spectroscopy—methods and applications," 1995, 1 cover page and 1 publishing page, published jointly by VCH Verlagsgesellschaft mbH, Weinheim (Federal Republic of Germany) and VCH Publishers, Inc., New York, N.Y. (USA).

Tam, Felicia, et al., "Plasmonic enhancement of molecular fluorescence," Nano Letters, 2007, pp. 496-501, vol. 7, No. 2, American Chemical Society.

Wang, Hui, et al., "Nanosphere arrays with controlled sub-10-nm gaps as surface-enhanced raman spectroscopy substrates," J. Am. Chem. Soc., 2005, pp. 14992-14993, vol. 127, No. 43, American Chemical Society.

Wang, Hui, et al., "Plasmonic nanoparticle heterodimers in a semiembedded geometry fabricated by stepwise upright assembly," Nano Letters, 2006, pp. 2945-2948, vol. 6, No. 12, American Chemical Society.

Wang, Hui, et al., "Plasmonic nanostructures: artificial molecules," Accounts of Chemical Research, 2007, pp. 53-62, vol. 40, No. 1, American Chemical Society.

Zhou, Qun, et al., "Charge transfer between metal nanoparticles interconnected with a functionalized molecule probed by surface-enhanced raman spectroscopy," Angew. Chem. Int. Ed., 2006, pp. 3970-3973, vol. 45, Wiley-VCH Verlag GmbH & Co. KGaA, Weinheim.

Office Action (Final) dated Jan. 5, 2011 (16 pages), U.S. Appl. No. 11/765,862, filed Jun. 20, 2007.

Al-Rawashdeh, Nathir, et al., "UV/visible and infrared spectra of polyethylene/nanoscopic gold rod composite films: effects of gold particle size, shape and orientation," NanoStructured Materials, 1997, pp. 383-386, vol. 9, Elsevier Science Ltd, Acta Metallurgica Inc.

Angel, S. M., et al., "Near-infrared surface-enhanced raman spectroscopy. Part II: copper and gold colloids," Applied Spectroscopy, 1989, pp. 367-372, vol. 43, No. 3, Society for Applied Spectroscopy.

Aslan, Kadir, et al., "Metal-enhanced fluorescence: an emerging tool in biotechnology," Biotechnology, 2005, pp. 55-62, vol. 16, Elsevier Ltd.

Badilescu, Simona, et al., "Enhanced infrared ATR spectra of o-, m-, and p-nitrobenzoic acid with Ag films," Applied Spectroscopy, 1989, pp. 549-552, vol. 43, No. 3, Society for Applied Spectroscopy.

Barnes, William L., et al., "Surface plasmon subwavelength optics," Nature, Aug. 14, 2003, pp. 824-830, vol. 424, Nature Publishing Group.

Brandl, Daniel W., et al., "Plasmon modes of nanosphere trimers and quadrumers," J. Phys. Chem. B, 2006, pp. 12302-12310, vol. 110, No. 25, American Chemical Society.

Cao, Linyou, et al., "Surface-enhanced raman scattering of p-aminothiophenol on a Au(core)/Cu(shell) nanoparticle assembly," ChemPhysChem, 2005, pp. 913-918, vol. 6, Wiley-VCH Verlag GmbH & Co. KGaA, Weinheim.

Cao, Yunwei Charles, et al., "Nanoparticles with raman spectroscopic fingerprints for DNA and RNA detection," www.sciencemag.org, Aug. 30, 2002, pp. 1536-1540, vol. 297, Science.

Chase, D. B., et al., "Surface-enhanced raman spectroscopy in the near-infrared," Applied Spectroscopy, 1988, pp. 1186-1187, vol. 42, No. 7, Society for Applied Spectroscopy.

Crookell, A., et al., "Surface-enhanced fourier transform raman spectroscopy in the near infrared," Chemical Physics Letters, Aug. 12, 1988, pp. 123-127, vol. 149, No. 2, Elsevier Science Publishers B.V. (North-Holland Physics Publishing Division).

Ebbesen, T. W., et al., "Extraordinary optical transmission through sub-wavelength hole arrays," Nature, Feb. 12, 1998, pp. 667-669, vol. 391, Macmillan Publishers Ltd.

Elghanian, Robert, et al., "Selective colorimetric detection of polynucleotides based on the distance-dependent optical properties of gold nanoparticles," www.sciencemag.org, Aug. 22, 1997, pp. 1078-1081, vol. 277, Science.

Foreign communication from the priority application—International Preliminary Report on Patentability, PCT/US2007/077389, Mar. 3, 2009, 6 pages.

Foreign communication from the priority application—International Search Report and Written Opinion, PCT/US07/77389, Jan. 29, 2008, 6 pages.

Genov, Dentcho A., et al., "Resonant field enhancements from metal nanoparticle arrays," Nano Letters, 2004, pp. 153-158, vol. 4, No. 1, American Chemical Society.

Goutev, Nikolay, et al., "Attenuated total reflection surface-enhanced infrared absorption spectroscopy of carboxyl terminated self-assembled monolayers on gold," Applied Spectroscopy, 2003, pp. 506-513, vol. 57, No. 5, Society for Applied Spectroscopy.

Haes, Amanda, J., et al., "Plasmonic materials for surface-enhanced sensing and spectroscopy," www.mrs.org/publications/bulletin, May 2005, pp. 368-375, vol. 30, MRS Bulletin.

Halas, Naomi, "Playing with plasmons: tuning the optical resonant properties of metallic nanoshells," www.mrs.org/publications/bulletin, May 2005, pp. 362-367, vol. 30, MRS Bulletin.

Hartstein, A., et al., "Enhancement of the infrared absorption from molecular monolayers with thin metal overlayers," Physical Review Letters, Jul. 21, 1980, pp. 201-204, vol. 45, No. 3, The American Physical Society.

Heaps, David A., et al., "Band shapes in the infrared spectra of thin organic films on metal nanoparticles," Vibrational Spectroscopy, 2006, pp. 45-50, vol. 42, Elsevier B.V.

Heaps, David A., et al., "Effect of molecular spacers on surface-enhanced attenuated total reflection infrared spectra of bulk liquids," Vibrational Spectroscopy, 2006, pp. 221-224, vol. 41, Elsevier B.V.

Jensen, T. R., et al., "Surface-enhanced infrared spectroscopy: a comparison of metal island films with discrete and nondiscrete surface plasmons," Applied Spectroscopy, 2000, pp. 371-377, vol. 54, No. 3, Society for Applied Spectroscopy.

Johnson, Eric, et al., "Surface-enhanced infrared spectroscopy of monolayers," J. Phys. Chem., 1995, pp. 9325-9330, vol. 99, No. 23, American Chemical Society.

Johnson, S. A., et al., "Application of surface-enhanced infrared absorption spectroscopy as a sensor for volatile organic compounds," Applied Spectroscopy, 1997, pp. 1423-1426, vol. 51, No. 9, Society for Applied Spectroscopy.

Kellner, R., et al., "Surface-enhanced vibrational spectroscopy: a new tool in chemical IR sensing?" Applied Spectroscopy, 1997, pp. 495-503, vol. 51, No. 4, Society for Applied Spectroscopy.

Krauth, Oliver, et al., "Anomalous infrared transmission of adsorbates on ultrathin metal films: Fano effect near the percolation threshold," Journal of Chemical Physics, Oct. 15, 2000, pp. 6330-6333, vol. 113, No. 15, American Institute of Physics.

Krauth, O., et al., "Asymmetric line shapes and surface enhanced infrared absorption of CO adsorbed on thin iron films on MgO(001)," Journal of Chemical Physics, Feb. 8, 1999, pp. 3113-3117, vol. 110, No. 6, American Institute of Physics.

Kreibig, Uwe, et al., "Optical properties of metal clusters," Jul. 7, 1995, 4 pages, Springer. Description of book from Amazon.com.

Lal, Surbhi, et al., "Profiling the near field of a plasmonic nanoparticle with raman-based molecular rulers," Nano Letters, 2006, pp. 2338-2343, vol. 6, No. 10, American Chemical Society.

Lee, Seung Joon, et al., "Hot spots in silver nanowire bundles for surface-enhanced raman spectroscopy," J. Am. Chem. Soc., 2006, pp. 2200-2201, vol. 128, No. 7, American Chemical Society.

Levin, Carly S., et al., "Determining the conformation of thiolated poly(ethylene glycol) on Au nanoshells by surface-enhanced Raman scattering spectroscopic assay," Analytical Chemistry, May 15, 2006, pp. 3277-3281, vol. 78, No. 10, American Chemical Society.

Li, Kuiru, et al., "Self-similar chain of metal nanospheres as an efficient nanolens," Physical Review Letters, Nov. 28, 2003, pp. 227402-1 to 227402-4, vol. 91, No. 22, The American Physical Society.

Maier, Stefan A., et al., "Plasmonics—a route to nanoscale optical devices," Advanced Materials, Oct. 2, 2001, pp. 1501-1505, vol. 13, No. 19, Wiley-VCH Verlag GmbH, D-69469 Weinheim.

Maier, Stefan A., et al., "Plasmonics: localization and guiding of electromagnetic energy in metal/dielectric structures," Journal of Applied Physics, 2005, pp. 011101-1 to 011101-10, vol. 98, American Institute of Physics.

Makino, Nobuaki, et al., "Characterization of surface contaminants by a silver film-enhanced IR—Johnson method," Applied Spectroscopy, 1997, pp. 1460-1463, vol. 51, No. 10, Society for Applied Spectroscopy.

McNutt, A., et al., "RAIRS Investigations on the orientation and intermolecular interactions of adenine on Cu(110)," Surface Science, 2003, pp. 131-144, vol. 531, Elsevier Science B.V.

Merklin, Gregory T., et al., "Influence of chemical interactions on the surface-enhanced infrared absorption spectrometry of nitrophenols on copper and silver films," Langmuir, 1997, pp. 6159-6163, vol. 13, No. 23, American Chemical Society.

Michaels, Amy M., et al., "Ag nanocrystal junctions as the site for surface-enhanced raman scattering of single rhodamine 6G molecules," J. Phys. Chem. B, 2000, pp. 11965-11971, vol. 104, No. 50, American Chemical Society.

Michaels, Amy M., et al., "Surface enhanced raman spectroscopy of individual rhodamine 6G molecules on large Ag nanocrystals," J. Am. Chem. Soc., 1999, pp. 9932-9939, vol. 121, No. 43, American Chemical Society.

Nikoobakht, B., et al., "Self-assembly of gold nanorods," J. Phys. Chem. B, 2000, pp. 8635-8640, vol. 104, No. 36, American Chemical Society.

Office Action dated Dec. 16, 2010 (19 pages), U.S. Appl. No. 12/439,251, filed Jul. 16. 2009.

Orendorff, Christopher J., et al., "pH-triggered assembly of gold nanorods," Langmuir, 2005, pp. 2022-2026, vol. 21, No. 5, American Chemical Society.

Osawa, Masatoshi, "Dynamic processes in electrochemical reactions studied by surface-enhanced infrared absorption spectroscopy (SEIRAS)," Bull. Chem. Soc. Jpn., 1997, pp. 2861-2880, vol. 70, The Chemical Society of Japan.

Osawa, Masatoshi, et al., "In-situ and real-time surface-enhanced infrared study of electrochemical reactions," Applied Spectroscopy, 1997, pp. 512-518, vol. 51, No. 4, Society for Applied Spectroscopy.

Osawa, Masatoshi, "Surface-enhanced infrared absorption," Topics Appl. Phys., 2001, pp. 163-187, vol. 81, Springer-Verlag Berlin Heidelberg.

Osawa, Masatoshi, et al., "Surface-enhanced infrared spectroscopy: the origin of the absorption enhancement and band selection rule in the infrared spectra of molecules adsorbed on fine metal particles," 1993, pp. 1497-1502, vol. 47, No. 9, Society for Applied Spectroscopy.

Ozbay, Ekmel, "Plasmonics: merging photonics and electronics at nanoscale dimensions," www.sciencemag.org, Jan. 13, 2006, pp. 189-193, vol. 311, Science.

Provisional patent application entitled "Nanoshell aggregates as efficient substrate for surface enhanced infrared absorption spectroscopy (SEIRA)," by Nancy J. Halas, et al., filed Sep. 1, 2006 as U.S. Appl. No. 60/842,089.

Pendry, J. B., "Negative refraction makes a perfect lens," Physical Review Letters, Oct. 30, 2000, pp. 3966-3969, vol. 85, No. 18, The American Physical Society.

Priebe. A., et al., "The correlation between film thickness and adsorbate line shape in surface enhanced infrared absorption," Sep. 1, 2003, pp. 4887-4890, vol. 119, No. 9, American Institute of Physics.

Advisory Action dated Mar. 2, 2011 (5 pages), U.S. Appl. No. 11/765,862, filed Jun. 20, 2007.

Advisory Action dated May 27, 2011 (4 pages), U.S. Appl. No. 121439,251, filed Jul. 16, 2009.

Office Action dated May 20, 2011 (25 pages), U.S. Appl. No. 11/765,862, filed Jun. 20, 2007.

* cited by examiner

ALL OPTICAL NANOSCALE SENSOR

CROSS-REFERENCE TO RELATED APPLICATIONS

The present application claims priority to U.S. Provisional Patent Application Ser. No. 60/804,793 filed Jun. 14, 2006 and entitled "All Optical Nanoscale pH Meter."

STATEMENT REGARDING FEDERALLY SPONSORED RESEARCH OR DEVELOPMENT

This invention was made with government support under grant number EEC-0304097, AFOSR F49620-03-C-0068, awarded by the National Science Foundation (NSF), under grant number C-1220, awarded by the Robert A. Welch Foundation, under grant number W911NF-04-01-0203, awarded by the Multidisciplinary University Research Initiative (MURI) of the Department of Defense, and under grant number DAMD17-03-1-0384 awarded by the Department of Defense Breast Cancer Research Program. The government has certain rights in the invention.

BACKGROUND

The development of active nanostructures, capable of performing a function or executing a specific task, is currently a major focus of research efforts in nanotechnology. One already highly successful nanodevice paradigm is the nanosensor: a designed nanostructure, which when addressed either optically or electrically, responds by providing information about its local environment through its optical or electrical response. All-optical nanosensors hold exceptional promise as embeddable nanodevices that could potentially be used to probe a variety of exceedingly complex environments, such as individual living cells or the human body, in a virtually noninvasive manner. In addition to passive and active functions, there is a third, "informative" role, for which metallic nanoparticles are particularly well suited, and which enables nanosensor development. Metal nanostructures, when excited on their plasmon resonance, give rise to high intensity electromagnetic fields at their surfaces which can be harnessed for chemically specific sensing functionalities. Metallic nanoparticles can be designed to enhance the spectroscopic response of molecules bound to, or in close proximity of, their surfaces, an effect known as surface enhanced Raman scattering (SERS). Detailed local chemical information can be retrieved from the spectrum of the inelastically scattered light from the nanoparticle complex. Thus, it would be desirable to develop an all-optical nanosensing device.

SUMMARY

Disclosed herein is a composition comprising a nanoparticle and at least one adsorbate associated with the nanoparticle, wherein the adsorbate displays at least one chemically responsive optical property.

Also disclosed herein is a method comprising associating an adsorbate with a nanoparticle, wherein the nanoparticle comprises a shell surrounding a core material with a lower conductivity than the shell material and the adsorbate displays at least one chemically responsive optical property, and engineering the nanoparticle to enhance the optical property of the adsorbate.

Further disclosed herein is a method comprising determining an optical response of an adsorbate associated with a nanoparticle as a function of a chemical parameter, and parameterizing the optical response to produce a one-dimensional representation of at least a portion of a spectral window of the optical response in a high dimensional vector space.

Further disclosed herein is a method comprising introducing an adsorbate associated with a nanoparticle to an environment of having an unknown chemical parameter, wherein the adsorbate comprises an optical response that is a function of the chemical parameter, acquiring the optical response of the adsorbate associated with a nanoparticle in the unknown environment, and determining the chemical parameter of the unknown environment based on a comparison of the optical response of the adsorbate in a known environment to the optical response of the adsorbate in the unknown environment.

Further disclosed herein is a method comprising introducing an adsorbate associated with a nanoparticle to an environment of unknown pH, wherein the adsorbate comprises a chemically responsive SERS spectral response that is a function of pH, acquiring the SERS spectral response of the adsorbate associated with a nanoparticle in the environment of unknown pH, and determining the pH of the unknown environment based on a comparison of the pH-dependent SERS spectral response of the adsorbate in a known environment to the SERS spectrum of the adsorbate in the unknown environment.

BRIEF DESCRIPTION OF THE DRAWINGS

FIG. 2$a$ is a plot of SERS spectra of para-mercaptobenzoic acid on a nanoshell at various pH values ranging from pH 4.0 to 9.0 in steps of 0.5 pH units.

FIG. 2$b$ depicts the repetitive cycling of the pH-sensitive optical sensor of Example 1 measured by monitoring the change in $I_{(COO-)}/I_{(C=O)}$ (1702 cm$^{-1}$/1393 cm$^{-1}$) Stokes mode.

FIG. 3$a$ depicts the spectral changes that form a manifold (one-dimensional curve) in $R^N$ that is indexed by pH where N is the number of spectral bands measured.

FIG. 3$b$ is a plot of the magnitude of the average error in the cross validation estimation procedure for the samples from Example 1.

FIG. 3$c$ is a plot of the average of the cross validation estimates in Example 1 where the error bars represent one standard deviation in the cross validation estimates.

DETAILED DESCRIPTION

Disclosed herein are nanoparticles comprising a dielectric core, a conducting shell, and an adsorbate. Each of these will be described in more detail later herein. In some embodiments, the core comprises silicon dioxide and the shell comprises at least one metal. The adsorbate may be any material that displays chemically sensitive optical properties. In an embodiment, the adsorbate displays pH-sensitive optical properties, and the nanoparticle may function as a pH-sensitive device capable of providing information on the pH of an environment and/or alterations in the pH of an environment. Hereinafter a nanoparticle having an adsorbate displaying pH-sensitive optical properties is referred to as a pH-sensitive optical sensor (POS).

In an embodiment, the POS comprises a nanoparticle. The nanoparticles of this disclosure may comprise at least two layers. At least one layer is immediately adjacent to and surrounds another layer. The innermost layer is termed the core. The layer that surrounds the core is termed the shell layer. The shell layer may be metallic in nature in that it is comprised of a material that is electrically conductive such as for example a metal or metal-like material. In some embodiments, at least one shell layer readily conducts electricity. Alternatively, at least one shell layer may have a lower dielectric constant than the adjacent inner or core layer. In some embodiments, this metal or metal-like shell layer is the outermost layer. In other embodiments, the shell layer immediately adjacent to the core is not the outer most shell layer. Additional layers, such as a non-conducting layer, a conducting layer, or a sequence of such layers, such as an alternating sequence of non-conducting and conducting layers, may be bound to this shell layer. Thus, for the purposes of this disclosure the term conductor is defined by reference to the adjacent inner layer and includes any material having a lower dielectric constant than its immediately adjacent inner layer.

In an embodiment, the adjacent inner or core layer to the shell layer is a non-conducting layer. Specifically contemplated are non-conducting layers made of dielectric materials and semiconductors. Suitable dielectric materials include but are not limited to silicon dioxide, titanium dioxide, polymethyl methacrylate (PMMA), polystyrene, gold sulfide and macromolecules such as dendrimers.

In an embodiment, the nanoparticle comprises a nonconducting core layer which may be a monodisperse, spherical particle that is easily synthesized in a wide range of sizes, and has a surface that can be chemically derivatized. In some embodiments, the core is spherical in shape; alternatively the core may have other shapes such as cubical, cylindrical, ellipsoidal, or hemispherical. Regardless of the geometry of the core, the particles may be homogenous in size and shape.

In an embodiment, the nonconducting layer or core material comprises monodisperse colloidal silica. In an embodiment, the nanoparticle comprises a conducting shell layer comprising a metallic material. Alternatively, the conducting layer comprises an organic conducting material such as polyacetylene, doped polyanaline and the like. Any metal that can conduct electricity may be suitable for use in this disclosure such as noble or coinage metals. Other examples of suitable metals include but are not limited to gold, silver, copper, platinum, palladium, lead, iron or the like and combinations thereof. Alternatively, the conducting layer comprises gold, silver or combinations thereof. Alloys or non-homogenous mixtures of such metals may also be used. The conducting shell layers may have a thickness that ranges from approximately 1 to 100 nm. The thickness of the shell material may be selected to generate a plasmon resonance frequency. They may coat the adjacent inner layer fully and uniformly or may partially coat that layer with atomic or molecular clusters. In either embodiment, at least approximately 30% of the adjacent inner layer is coated by the conducting layer. Such nanoparticles comprising a non-conductive inner core and an electrically conductive outer shell and methods of engineering said particles such that they generate a plasmon resonance frequency are described in U.S. Pat. Nos. 6,344,272; 6,699,724; and 7,147,687 each of which are incorporated by reference herein in its entirety.

Hereinafter, for simplicity, the disclosure will focus on the use of nanoparticles comprising spherical or elliptical shells (i.e., nanoshells) as the nanoparticles in the POS however, other nanoparticles such as for example hollow nanoshells, multilayer nanoshells, nanorods, nanostars, nanotriangles, nanocubes, individual nanospheres, and aggregates of nanospheres are also contemplated.

In an embodiment, the POS comprises at least one adsorbate. The adsorbate may be any material that can associate with the nanoparticles of this disclosure and displays chemically sensitive optical properties, for example a material that displays a chemically sensitive SERS spectrum. In an embodiment, the adsorbate displays pH-sensitive optical properties, for example any material that displays a pH-sensitive SERS spectrum. The adsorbate may be further characterized by the presence of features that allow for enhanced optical properties such as for example aromatic rings, lone pair electrons and the like. In an embodiment, the adsorbate contains one or more pH sensitive functional groups such as carboxylic acids. Examples of suitable adsorbates include without limitation para-mercaptobenzoic acid (pMBA), ortho-mercaptobenzoic acid (oMBA), meta-mercaptobenzoic acid (mMBA), para-mercaptophenylacetic acid or combinations thereof. The majority of the disclosure herein focuses on an embodiment wherein the optically responsive chemical parameter of the adsorbate is pH, with the understanding that other chemical parameters such as identity, concentration, etc. may be employed. For example, an optical response such as a SERS spectral response may be a function of other chemical parameters such as chemical identity, chemical concentration, etc.

The adsorbate may be able to associate with the nanoparticles through any number and type of interaction. As such, although the term adsorbate is used throughout the disclosure, a variety of mechanisms in addition to adsorption may be contemplated as mechanisms of associating the adsorbate with the nanoshell. For example, the adsorbate may associate with the nanoshells through an electrostatic interaction with the shell layer. Alternatively, the adsorbate may associate with the nanoshells through the formation of a chemical bond between the adsorbate and the components of the shell layer. Alternatively, the adsorbate may associate with the nanoshells through a plurality of interactions comprising chemical bonding, electrostatic interactions, physical interactions or combinations thereof.

In an embodiment, the adsorbate is present in sufficient quantity to allow for the adsorbate to cover from about 1% to about 100% of the surface area of the nanoshell, alternatively the adsorbate covers greater than about 5, 10, 15, 20, 25, 30, 35, 40, 45, 50, 55, 60, 65, 70, 75, 80, 85, 90, or 95% of the surface area of the nanoshell. In an embodiment, the adsorbate covers about 100% of the surface of the nanoshells. A method for the preparation of such a POS may comprise chemically bonding an adsorbate to a nanoshell wherein an excess of adsorbate to nanoshell surface area is present in order to facilitate complete coverage of the surface area of the nanoshell. The method may further comprise additional processing of the POS following association of the nanoshell with an excess of adsorbate (e.g. rinsing) so as to facilitate the removal of any adsorbate not chemically bound to the nanoshell. Methods of chemically bonding the adsorbate to the POS will vary depending on the nature of the adsorbate and the type and number of bonds to be formed and may be chosen by one of ordinary skill in the art to meet the desired needs of the process. Techniques for chemically bonding the pMBA adsorbate to a gold nanoshell are described later herein. In some embodiments, the POS comprises more than one adsorbate. The adsorbate may be chosen to provide non-interfering pH-sensitive optical properties over a wide pH range. Alternatively, the adsorbate may have more than one pH-sensitive functional group with various $pK_a$s.

Figure 1:
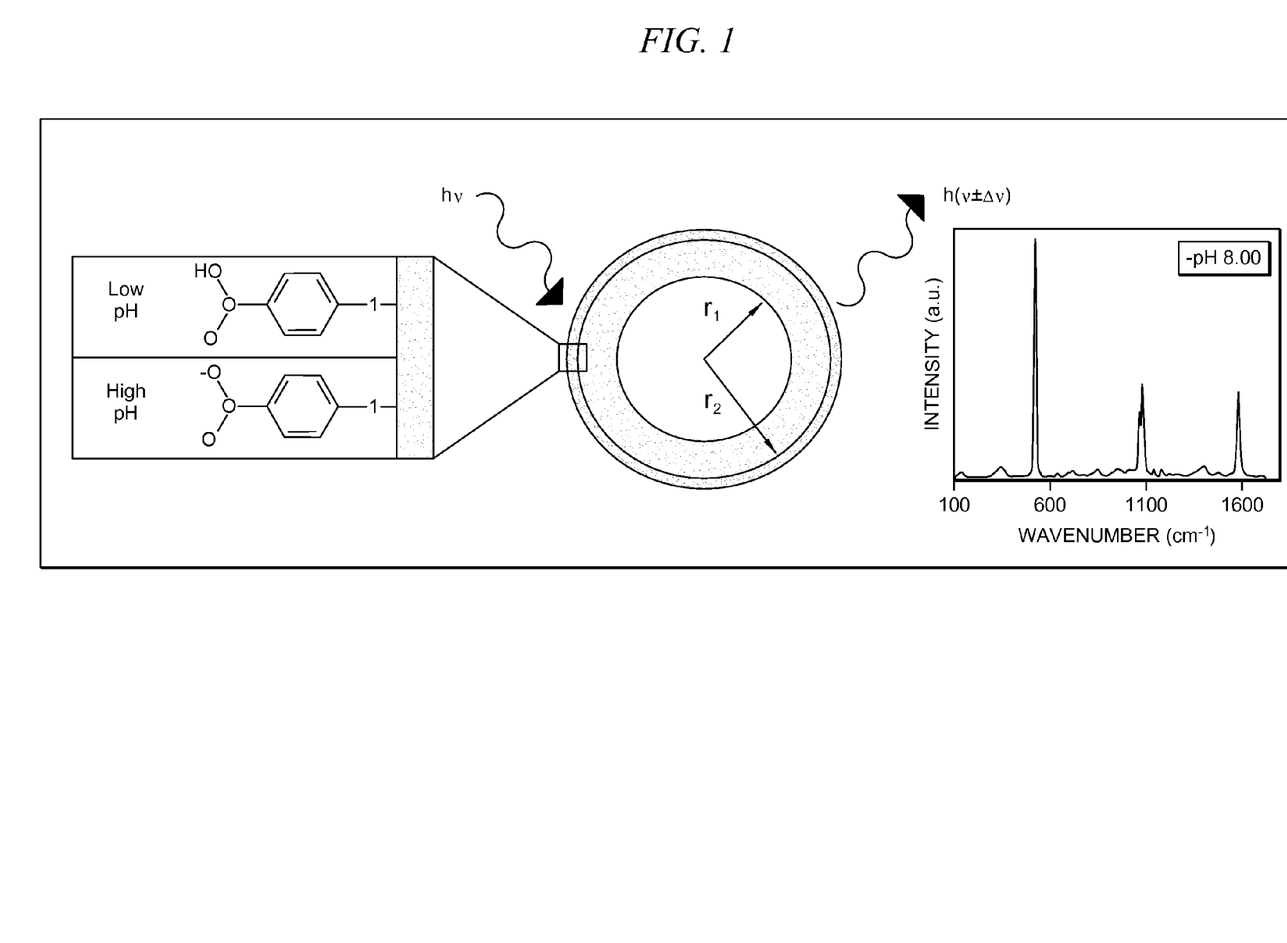
FIG. 1 is a schematic diagram of a Au nanoshell pH sensor.

In an embodiment, the nanoshell and adsorbate are chosen by one of ordinary skill in the art such that the nanoshell is engineered to enhance the SERS spectra of the adsorbate. Without wishing to be limited by theory, the plasmon resonances of the metallic shell may provide intense, local optical-frequency fields responsible for SERS. A striking example of this is the series of experiments reporting enormous SERS enhancements of $10^{12}$-$10^{15}$ for dye molecules adsorbed on surfaces of aggregated Au and Ag colloid films. Isolated solid nanoshells at their respective plasmon resonance (~525 nm for gold, ~430 nm for silver) have reported enhancement factors up to $10^6$. Herein, the individual nanoshells may have a plasmon resonance frequency that is between a first frequency of an incident electromagnetic radiation and a second frequency of Raman response from the adsorbate and that may lead to significant enhancements of the SERS response of the adsorbate. Methods of engineering the nanoshell to enhance the SERS spectra of the adsorbate have been described in U.S. patent application Ser. No. 11/573,365, which is incorporated by reference herein in its entirety. One example of a POS is shown in FIG. 1. FIG. 1 depicts a gold nanoshell pH sensor consisting of nanoshells with core radius $r_1$=55 nm, a total nanoshell radius $r_2$=71 nm, and an adsorbed monolayer of pMBA. The pMBA molecule on a gold nanoshell yields a pH-dependent SERS spectrum.

In some embodiments, the POS may be employed in methodologies to be described in more detail later herein as individual particles, wherein the particles may be supported or unsupported. For example, the POS may comprise one or more nanoshells having an associated adsorbate affixed to the surface of a support material. Any support material compatible with the user desired process may be employed. For example, the support may comprise an inorganic oxide such as the oxides of silicon or aluminum.

In an embodiment, a method of using the POS of this disclosure comprises acquiring the SERS spectrum of the adsorbate as a function of pH. The resulting data may provide the SERS spectral response of the adsorbate as a function of pH. In some embodiments, the pH may range from about 0 to about 14, alternatively from about 5 to about 10, alternatively from about 5.8 to about 7.6. In some embodiments, the pH may assume any range compatible with the components of the POS. The SERS spectrum may be detected using any device known in the art for the acquisition of such spectra. For example, the SERS spectrum may be detected utilizing an inVia Raman microscope commercially available from Renishaw, United Kingdom. The excitation wavelength may be chosen to be compatible with the plasmon resonance of the nanoshells described herein. As such no particular limitation is placed on the excitation wavelength which may be chosen by one of ordinary skill in the art to meet the desired application.

The spectra may be acquired manually, alternatively the spectra may be acquired automatically and the information conveyed to a computerized apparatus, wherein the method described herein is implemented in software on a general purpose computer or other computerized component having a processor, user interface, microprocessor, memory, and other associated hardware and operating software. Software implementing the method may be stored in tangible media and/or may be resident in memory, for example, on a computer. Likewise, the spectral data acquired may be stored in a tangible media, computer memory, hardcopy such as a paper printout, or other storage device.

In an embodiment, a method of determining the pH of an environment comprises introducing to said environment of unknown pH a POS of the type described herein. The SERS spectrum of the adsorbate in said environment may then be compared to the SERS spectrum at one or more known pH values and the comparison used to determine or estimate the pH of the environment. In an alternative embodiment, the SERS spectral data acquired at known pH values may be processed (e.g. parameterized or correlated) to allow for a more facile comparison to similar SERS spectral data collected for samples having an unknown pH value.

In an embodiment, the data acquired (e.g., the SERS spectral response at a plurality of known pH values) may be parameterized to allow a user to visualize at least a portion of the spectral window of the pH-induced SERS spectral response as plurality of points on a one-dimensional curve (known as a manifold) in a high dimensional vector space. Each dimension of this high dimensional space corresponds to one frequency band of the measured SERS spectral response. The nonlinear data points may then be fit to a plurality of linear segments (called a locally linear manifold approximation) using any number of software programs capable of providing a user-desired fit to a nonlinear data set such as for example MATLAB. Approximating the data points on the one-dimensional manifold using linear segments can be carried out employing any technique known to one of ordinary skill in the art, including for example ISO-MAP which is described in Tenenbaum et al. entitled "A Global Geometric Framework for Nonlinear Dimensionality Reduction" published in Science; Volume 290; pages 2319-2322 or local linear embedding which is described by Roweis et al. entitled "Nonlinear Dimensionality Reduction by Locally Linear Embedding" published in Science; Volume 290; pages 2323-2326, both of which are incorporated by reference in their entirety. Alternatively, the measured data points along this one-dimensional manifold can be approximated locally by linear segments found through standard least-squares data fitting. For example, the nonlinear data fit may be carried out by the application of x linear segments having k breakpoints to curve z. The number and placement of the breakpoints may be chosen by one of ordinary skill in the art to provide a best fit to the nonlinear data. Given these breakpoints, linear segments can be fit to the data using standard least-squares techniques applied in the high-dimensional dimensional space. The fitting of the linear segments, the number of breakpoints, and the position of the breakpoints may be carried out using the previously mentioned software. The parameterization of the pH-dependent SERS spectral response of the adsorbate as disclosed herein may provide a pH resolution of about 0.10 pH units over the range of the device. It is to be understood that the pH resolution may vary depending on a number of factors including the nature of the adsorbate and the pH window chosen.

In an embodiment, the SERS spectrum of a sample of unknown pH may be recorded and then compared to the locally linear manifold approximation made of the data acquired at one or more known pH values and represented as a graph having the features previously described herein. The closest point on the locally linear manifold approximation may be located and then (since it is parameterized by pH units), the pH estimate may be read directly from the graph.

A POS of this disclosure may function as an all optical pH sensor with the ability to detect and report pH-dependent changes over a wide pH range. The POS may comprise an individual particle whose pH-dependent SERS spectral response is detectable in the absence of an aggregate of particles. The POS may provide a means to monitor pH alterations in various environments using a biocompatible wireless device. In an embodiment, the POS functions as a nanosensor that may be embedded in an organism whose tissues or cells are experiencing a dysfunction or disorder. The POS may be localized to specific cellular types such as for example neoplastic cells or cells having comprised cellular functions and may provide a means of measuring pH and/or pH alterations in said environments. For example, a POS may be introduced to a cellular environment and the Raman spectra of the adsorbate acquired utilizing excitation by a laser device in vivo with subsequent detection of the SERS spectrum of the adsorbate. The SERS spectrum of the adsorbate may be detected by a device located in vivo in proximity to the POS and capable of receiving and transmitting SERS spectral data.

In other embodiments, the POS may be introduced to an organ or cell that has been transplanted into a host organism and may provide information on pH or pH alterations in said organ or cell that may be used to diagnose dysfunctions or disorders such as for example early stage transplant rejection. In yet other embodiments, the POS may be employed as a pH-sensitive detector in vitro. Additional uses for the POS of this disclosure would be apparent to one of ordinary skill in the art.

The following references provide background information and are each incorporated herein by reference, except to the extent that they define terms differently than those terms are defined herein:

1. Clark, H. A.; Barker, S. L. R.; Brasuel, M. Miller, M. T.; Monson, E.; Parus, S.; Shi, Z.-Y.; Song, A.; Thorsrud, B.; Kopelman, R.; Ade, A.: Meixner, W.; Athey, B.; Hoyer, M.; Hill, D.; Lightle, R.; Philbert, M. A., Subcellular optochemical nanobiosensors; probes encapsulated by biologically localised embedding (PEBBLEs). *Sensors and Actuators B* 1998, 51, 12-16.
2. Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S., Quantum dots for live cells, in vivo imaging, and diagnostics. *Science* 2005, 307, 538-544.
3. Oldenburg, S. J.; Averitt, R. D.; Westcott, S. L.; Halas, N. J., Nanoengineering of optical resonances. *Chem. Phys. Lett.* 1998, 288, 243-247.
4. Prodan, E.; Radloff, C.; Halas, N. J.; Nordlander, P. A., A hybridization model for the plasmon response of complex nanostructures. *Science* 2003, 302, 419-422.
5. Chen, J.; Saeki, F.; Wiley, B. J.; Cang, H.; Cobb, M. J.; Li, Z.-Y.; Au, L.; Zhang, H.; Kimmey, M. B.; Li, X. D.; Xia, Y., Gold Nanocages: Bioconjugation and Their Potential Use as Optical Imaging Contrast Agents. *Nano Lett.* 2005, 5, 473-377.
6. Huang, X. H.; El-Sayed, I. H.; Qian, W.; El-Sayed, M. A., Cancer cells imaging and photothermal therapy in the near-infrared region by using gold nanorods. *J. Am. Chem. Soc.* 2006, 128, 2115-2120.
7. O'Neal, D. P.; Hirsch, L. R.; Halas, N. J.; Payner, J. D.; West, J. L., Photothermal Tumor Ablation in mice using near infrared absorbing nanoshells. *Cancer Letter* 2004, 209, 171-176.
8. Jeanmarie, D. L.; Van Duyne, R. P., Surface Raman Spectroelectrochemistry. Part I. Heterocyclic, Aromatic, and Aliphatic Amines Adsorbed on the Anodized Silver Electrode. *J. Electroanal. Chem.* 1977, 84, 1-20.
9. Moskovits, M., Surface-enhanced spectroscopy. *Rev. Mod. Phys.* 1985, 57, 783-826. Xu, S.; Ji, X.; Xu, W.; Zhao, B.; Dou, X.; Bai, Y.; Ozaki, Y., Surface-enhanced Raman scattering studies on immunoassay. *J. Biomed Opt.* 2005, 10, (3), 031112.
10. Jackson, J. B.; Halas N. J., Surface Enhanced Raman Scattering on tunable plasmonic nanoparticle substrates. *Proc. Nati. Acad. Sci.* 2004, 101, (52), 17930-17935.
11. Jackson, J. B.; Westcott, S. L.; Hirsch, L. R.; West, J. L.; Halas, N. J., Controlling the Surface Enhanced Raman Effect on the surface of a core-shell nanoparticle. *Appl. Phys. Lett.* 2003, 82, 257-259.
12. Michota, A.; Bukowska, J., Surface-enhanced Raman scattering (SERS) of 4-mercaptobenzoic acid on silver and gold substrates. *J. Raman Spect.* 2003, 34, 21-25.
13. Lee, S. B.; Kim, K.; Kim, M. S., Surface-enhanced Raman scattering of o-mercaptobenzoic acid in silver sol. *J. Raman Spect.* 1991, 22, 811-817.
14. Talley, C. E.; Jusinski, L.; Hollars, C. W.; Lane, S. M.; Huser, T., Intracellular pH Sensors Based on Surface-Enhanced Raman Scattering. *Anal. Chem.* 2004, 76, 7064-7068.
15. Talley, C. E.; Jackson, J. B.; Oubre, C.; Grady, N.; Huser, T.; Hollars, C.; Lane, S.; Nordlander, P.; Halas, N. J., Surface Enhanced Raman Scattering from Individual Au Nanoparticles and Nanoparticle Dimer Substrates. *Nano Letters* 2005, 5, 18218-18222.
16. Clark, H. A.; Hoyer, M.; Philbert, M. A.; Kopelman, R., Optical Nanosensors for Chemical Analysis inside Single Living Cells. 1. Fabrication, Characterization, and Methods for Intracellular Delivery of PEBBLE Sensors. *Anal. Chem.* 1999, 71, 4831-4836.
17. Burges, C. J. C., Geometric Methods for Feature Extraction and Dimensional Reduction. *In Data Mining and Knowledge Discovery Handbook: A Complete Guide for Practitioners and Researchers*, L. Rokach and O. Maimon, S., Ed. 2005; pp. 59-92.
18. Ramakrishna, R. S.; Femandopulle, M. E., Complexes of thallium (I) and thallium (III) with thiosalicylic acid (o-mercaptobenzoic acid) and salicylic acid. *J. Inorg. Nuc. Chem.* 1971, 33, 1940-1942.
19. Martell, A. E.; Smith, R. M., *In Critical Stability Constants*. Plenum Press: New York, 1977. Joo, T. H.; Kim. K., Kim, M. S., Surface-Enhanced Raman Scattering (SERS) of 1-propanethiol in silver sol. *J. Phys. Chem.* 1986, 90, 5816-5819.
20. Moskovits, M.; Suh, J. S., The geometry of several molecular ions adsorbed on the surface of colloidal silver. *J. Phys. Chem.* 1984, 88, 1293-1298.
21. Wells, M.; Dermody, D. L.; Yang, H. C.; Kim, T., Crooks, R. M.; Ricco, A. J., Interactions between Organized, Surface-Confined Monolayers and Vapor-Phase Probe Molecules. 9. Structure/Reactivity Relationship between Three Surface-Confined Isomers of Mercaptobenzoic Acid and Vapor-Phase Decylamine. *Langmuir* 1996, 12, 1989-1996.
22. Gao, P.; Weaver, M. J., Surface-enhanced Raman spectroscopy as a probe of adsorbate-surface bonding: benzene and monosubstituted benzenes adsorbed at gold electrodes. *J. Phys. Chem.* 1985, 89, 5040-5046.
23. Kwon, Y. J.; Son, D. H.; Ahn, S. J.; Kim, M. S.; Kim, K., Vibrational Spectroscopic Investigation of Benzoic Acid Adsorbed on Silver. *J. Phys. Chem.* 1994, 98, 8481-8487. Varsanyi, G., *Assignments for Vibrational Spectra of seven Hundred Benzene Derivatives*. Wiley: New York, 1974.
24. Osawa, M.; Matsuda, N.; Yoshii, K.; Uchida, I., Charge transfer resonance Raman process in surface-enhanced Raman scattering from p-aminothiophenol adsorbed on silver: Herzberg-Teller contribution. *J. Phys. Chem.* 1994, 98, 12702-12707.
25. Smallbone, K.; Gavaghan, D. J.; Gatenby, R. A.; Maini, P. K., The role of acidity in solid tumour growth and invasion. *J. Theor. Bio.* 2005, 253, 476-484.
26. Roweis, S. T.; Saul, L. K., Nonlinear Dimensionality Reduction by Locally Linear Embedding. *Science* 2000, 290, 2323-2326.
27. Hardle, W., *Applied Nonparametric Regression*. Cambridge University Press: Cambridge, U. K., 1990.

28. Vaupel, P.; Kallinowski, F.; Okunieff, P., Blood flow, oxygen and nutrient supply, and metabolic microenvironment of human tumors: a review. *Cancer Res.* 1989, 49, 6449-6465.

EXAMPLES

The various embodiments having been described, the following examples are given as particular embodiments and to demonstrate the practice and advantages thereof. It is understood that the examples are given by way of illustration and are not intended to limit the specification or the claims in any manner.

Example 1

A POS of the type disclosed herein was prepared and investigated as an all-optical pH sensor. Specifically, to construct this device, Au nanoshells were fabricated according to the protocols described by Oldenberg et al. "Nanoengineering of Optical Resonances" published in 1998 in *Chem. Phys. Lett.*; V288; pages 243-247 and incorporated by reference herein in its entirety. The nanoshell core and shell dimensions were adjusted so that the plasmon resonance provided a far-field absorbance maximum near 785 nm in $H_2O$, $[r_1, r_2]=[55, 71]$ nm, to provide surface enhanced Raman scattering enhancement at the 785 nm pump laser wavelength. Au nanoshells were immobilized by depositing a drop of aqueous nanoshells solution onto 3-aminopropyltriethoxy silane (APTES, Aldrich) coated silicon wafer supports (Addison Engineering Inc.) and allowing the water to evaporate. The electrostatic interaction between the nanoshells and the amine group resulted in dispersed nanoshells bound to the silicon. The anchored nanoshells were exposed to solutions of pMBA (Sigma Aldrich) presolubilized in ethanol and then diluted in Milli-Q water (Millipore) for one hour, then thoroughly rinsed with Milli-Q water. In order to measure the pH response, SERS spectra were measured from acidic to basic pH levels. Before acquiring Raman spectra at each pH, the sample was immersed in phosphate buffered saline (PBS) of pH adjusted to the desired value for 10 min. A Fisher Scientific Accumet AP63 portable pH meter was used to adjust the pH of the buffer to an accuracy of 0.01 pH units. Raman spectra were then recorded while the entire adsorbate was immersed in ambient buffer solution using a Renishaw inVia Raman microscope (Renishaw, United Kingdom) with 785 nm wavelength excitation and 55 µW power at the sample. Backscattered light was collected using a 63× water immersion lens (Leica, Germany) and high resolution spectra were acquired using a 30-sec integration time. Scans were collected from various spots on each silicon wafer, at each pH value. Between the Raman scans at different pH levels, samples were rinsed with Milli-Q water and incubated for 10 min. in fresh buffer at the new pH.

Figure 2A:
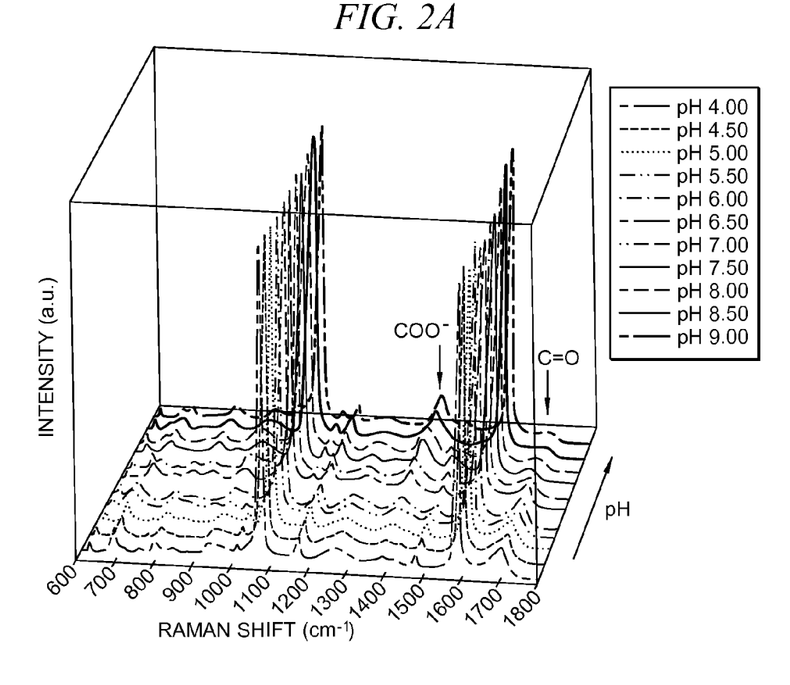
Figure 2B:
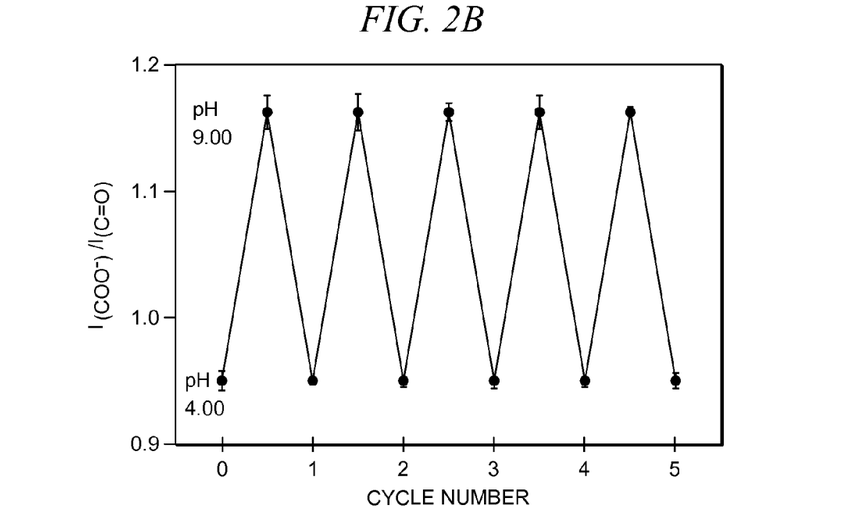

FIG. 2(*a*) shows the SERS spectra of the nanosensor as a function of pH, ranging from pH 4.0 to pH 9.0. The most prominent features in the SERS spectra are the Stokes features appearing at 1077 $cm^{-1}$ and 1590 $cm^{-1}$, assigned to the ring breathing and axial deformation modes of pMBA, respectively. As the pH of the nanoenvironment was changed from pH 4.0 to 9.0, highly reproducible spectral changes were observed in the SERS spectra. The most significant of these changes occurred at 1702 $cm^{-1}$ and 1394 $cm^{-1}$, attributable to the C=O and $COO^-$ stretching modes of pMBA, respectively. By monitoring the ratio of these two peaks, it was shown that this nanodevice can be cycled repeatedly from pH 4.0 to 9.0, where the ratio of the 1702 $cm^{-1}$ and 1394 $cm^{-1}$ peaks provides a simple optical readout for low resolution changes in local pH, see FIG. 2*b*. Referring to FIG. 2*b*, repetitive cycling of the Raman pH nanosensor was measured by monitoring the change in the $I(COO^-)/I(C=O)$ (1702 $cm^{-1}$/1393 $cm^{-1}$) Stokes modes. The intensities were measured with respect to that of the 1077 $cm^{-1}$ band to which spectra (at each pH) were normalized. Error bars represent the standard deviation for the measurements.

The highly complex changes in the SERS spectrum of this molecule that occurred over this very large pH range not only provided a great deal of information that can be used in assessing the device resolution, but are themselves of intrinsic fundamental interest. pMBA is a weak acid, and since a reduction in the $pK_a$ of acid molecules typically occurs upon covalent attachment to metal surfaces, it is expected that pMBA may still be partially protonated under significantly acidic conditions. The presence of dissociated carboxylate groups at low pH was indicated by the appearance of the broad $COO^-$ band at 1393 $cm^{-1}$, appearing much weaker than the C=O band at 1702 $cm^{-1}$. With increasing pH the number of dissociated carboxylate groups increases, enhancing the vibrational stretching mode of $COO^-$, resulting in an increase in mode intensity and a shift of the 1393 $cm^{-1}$ mode to higher wavenumbers. However, even at pH 9, the $COO^-$ band remains broad, suggesting that some pMBA molecules may still be involved in hydrogen bonding in addition to the possible interaction between $COO^-$ groups and the ring hydrogens. The low energy shoulder of the carbonyl mode at 1702 $cm^{-1}$ occurred most strongly at low pH, which indicated that some pMBA molecules might be participating in intramonolayer hydrogen bonding between adjacent pMBA molecules and/or between pMBA and the solution ambient. Multiple overlapping features in the broad 1393 $cm^{-1}$ $COO^-$ band are evident at low pH, which may possibly be attributable to hydrogen bonding between protonated and deprotonated carboxylate groups. From Gaussian calculations (DFT/B3LYP level) it can be inferred that such broadening could be caused by possible interactions between the carboxylate groups and the ring hydrogens. Interactions involving the $COO^-$, COOH and the ring hydrogens may be responsible for altering the $COO^-$ and C=O modes, resulting in the spectral broadening of this mode observed at acidic pH. Other spectral features in the pMBA SERS spectrum which also show pH-dependency include the nominally 1137 $cm^{-1}$ Stokes mode, predicted to be a CH in-plane bending mode, which undergoes noticeable spectral changes in intensity with increasing pH. The intensity of this weak mode increases with increasing pH, as does the mode appearing at 845 $cm^{-1}$. This latter spectral feature is assigned to $COO^-$ bending, and its spectral behavior closely resembles that of the $COO^-$ stretching mode at 1393 $cm^{-1}$. The spectral features at 696 $cm^{-1}$, 718 $cm^{-1}$, and 800 $cm^{-1}$ also show pH-dependent changes in intensity. With increasing pH, the intensity of the 696 $cm^{-1}$ band gradually decreases and that of the 718 $cm^{-1}$ band increases. The 696 $cm^{-1}$ mode was assigned in neutral pMBA (acidic limit) to a mixture of OCO bending, in-plane ring compression and C—S stretching. The mode at 718 $cm^{-1}$ was assigned to out-of-plane ring hydrogen wagging. In the basic limit, the deprotonated pMBA anion was found to have corresponding modes, only reversed in energy from the case of the protonated molecule. The 800 $cm^{-1}$ band appears to have a mixed vibrational nature of in-plane ring deformation motion, C—COOH stretching, and $COO^-$ bending, decreasing with increasing pH. Since the intensity of in-plane ring vibrational modes, such as that of the 1137 $cm^{-1}$ and the 718 $cm^{-1}$ bands, was seen to increase with increasing pH, it is proposed that the 800 $cm^{-1}$ band is dominated mainly by the C—COOH stretching vibration. Since the 696 cm$^{-1}$, 718 cm$^{-1}$, and 1137 cm$^{-1}$ features are all related to the benzene ring of the pMBA molecule, the pH-dependent change in the intensity of these bands may be related to the orientation of pMBA on the Au nanoshell surface. However, without wishing to be limited by theory, since saturation coverage of pMBA was present on the nanoshells, it is expected that the pMBA molecules are packed densely on the nanoshell surface in an upright configuration and undergo only minor reorientations with respect to surface normal over the pH range investigated.

In order to test the validity and accuracy of the POS, a finer data set was collected in increments of 0.2 pH units over a narrower pH range (5.80 to 7.60). This pH range was chosen due to its biological relevance, for example, within this pH range a distinction can be made between acidic cancer cells and healthy tissue. A simple ratio of pH-dependent SERS peaks extracted from the spectral output of the POS, see FIG. 2b, may be used to monitor large changes in pH, but in order to determine the usefulness of such a nanodevice in real applications, a quantitative understanding of the accuracy of its pH measurements across the working pH range of the device was obtained.

Figure 3A:
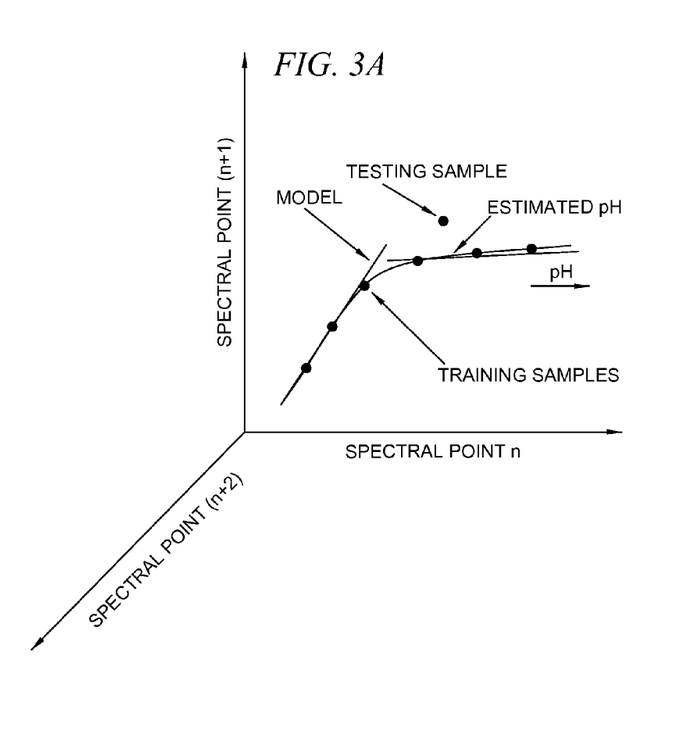

The POS was observed to display smooth changes in the measured SERS spectrum as a function of pH over the pH range of 5.8 to 7.6. Each measured spectrum was then considered as a point in an N-dimensional space ($R^N$), where N is the number of discrete points taken to acquire each SERS spectrum. Each axis in this abstract space indicates Raman frequency, with the value along each axis expressing the spectral energy at that frequency. Varying pH induces spectral changes that trace out a well-behaved one-dimensional trajectory in $R^N$ (parameterized by the pH value) that defines the relationship between the pH and the SERS spectra. FIG. 3a illustrates that the spectral changes form a manifold (one-dimensional curve) in $R^N$ that is indexed by pH, where N is the number of spectral bands measured. A locally linear approximation to the pH-Raman manifold was constructed by finding the best collection of straight line segments to fit a collection of training data samples (similar to the locally linear embedding algorithm).

Figure 3B:
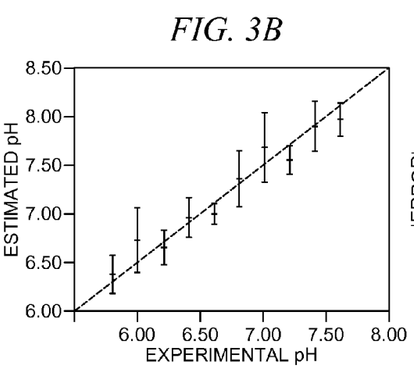
Figure 3C:
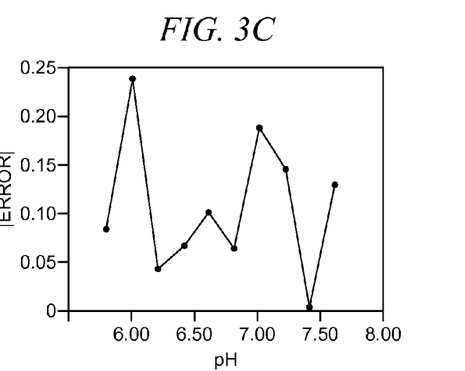

A series of pH-dependent SERS spectra served as "training" data with which the parameterization was tested. Each spectrum in this figure was constructed from the average of five SERS spectra taken at the same pH and at different regions on the wafer sample. Because the analysis depended only on the relative intensity at many different Raman frequencies ranging from 600 to 1800 cm$^{-1}$, each SERS spectrum was normalized to its value at a specific frequency, 1400 cm$^{-1}$. Since the relative changes in peak height were being examined, it did not matter where the baseline was chosen as long as there was no known contributing signal from the pMBA or possible contribution from the silicon support. To model the pH Raman manifold, the piecewise liner curve in $R^N$ with k segments that minimized the mean-squared error over the collection of training data was found. The (k-1) breakpoints were found by exhaustively searching all possible gaps between the training data pH values to find the breakpoints that produce the minimum mean-squared error fit. The best fitting linear segments were found using a standard least squares method applied in $R^N$. For the POS output, a two-segment piecewise linear curve was found to fit the pH manifold with high accuracy and minimal complexity. Cross-validation was used to judge the variation of the estimation procedure by testing each SERS spectrum against the parameterized manifold and the results of the cross-validation is shown in FIG. 3b. The cross-validation was accomplished by constructing the pH Raman manifold model using four of the five available spectra at each pH, and testing the variation between the fifth spectrum and the parameterized model. This procedure was repeated five times (leaving each scan out once) and the resulting pH estimates used to judge the accuracy and precision of the procedure. The magnitude of the average error over the pH range of the device was obtained, see FIG. 3c. The average magnitude across the working pH range was 0.10. However, this varied significantly across the pH range of the device, with a much larger error occurring around pH 6.0 than elsewhere in the pH range being evaluated. Without wishing to be limited by theory, the increased error in this specific range is attributed to an observed increase in spectral fluctuations for the SERS spectra for this specific pH which is likely to be near the effective $pK_a$ of the pMBA adsorbate molecules. It is quite possible that molecular fluctuations occurring at this pH due to protonation-deprotonation dynamics may give rise to the increased spectral noise observed, which translate to a lower accuracy for the POS at this specific region of its pH range.

The ultimate resolving power of the POS depended partially on the resolution of the training data used to model the pH Raman manifold. The resolving power of the POS built with training data at 0.20 pH intervals was further explored by utilizing the manifold approximation techniques to estimate the pH of two test samples taken between the training data pH values (having pH values of 6.10 and 7.15). The POS estimated the pH values of the samples to be 6.47 and 7.01 respectively. For the pH 6.10 test sample, the error was slightly larger than predicted by the cross-validation study. However, similar to what was observed with the training data, the larger error appeared in a pH range where increased SERS spectral fluctuations were observed.

While various embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference herein is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A composition comprising a nanoparticle and at least one adsorbate associated with the nanoparticle, wherein the adsorbate displays a chemically responsive surface enhanced Raman scattering (SERS) spectral response that is a function of pH over at least 5 pH units and wherein the adsorbate comprises more than one pH sensitive functional group.

2. The composition of claim wherein the nanoparticle comprises a shell surrounding a core material with a lower conductivity than the shell material, and the thickness of the core material and the shell material is engineered to generate a plasmon resonance frequency.

3. The composition of claim 1 wherein the nanoparticle comprises a spherical or elliptical shell, hollow nanoshell, multilayer nanoshell, nanorod, nanostar, nanotriangle, nanocube, individual atmospheres, nanosphere aggregates, or combinations thereof.

4. The composition of claim 1 wherein the adsorbate comprises para-mercaptobenzoic acid, ortho-mercaptobenzoic acid, meta-mercaptobenzoic acid, para-mercaptophenylacetic acid or combinations thereof.

5. The composition of claim 1 wherein the adsorbate is associated with the nanoparticle by an electrostatic interaction, by at least one chemical bond, by physical association, or combinations thereof.

6. The composition of claim 1 wherein the SERS response occurs over a pH range of from about 0 to about 14.

7. The composition of claim 1 wherein the composition is operable as a pH sensor.

8. A method comprising:
associating an adsorbate with a nanoparticle, wherein the nanoparticle comprises a shell surrounding a core material with a lower conductivity than the shell material and the adsorbate displays at least one chemically responsive optical property; and
engineering the nanoparticle to enhance the optical property of the adsorbate, wherein the chemically responsive optical property comprises a surface enhanced Raman scattering (SERS) spectral response that is a function of pH over at least 5 pH units and wherein the adsorbate comprises more than one pH sensitive functional group.

9. The method of claim 8 wherein engineering the nanoparticle comprises adjusting the aspect ratios of the nanoparticle, adjusting the components of the nanoparticle, adjusting the shape of the nanoparticle, adjusting the size of the nanoparticle, adjusting the shell thickness of the nanoparticle or combinations thereof.

10. A method comprising:
determining an optical response of an adsorbate associated with a nanoparticle as a function of a chemical parameter; and
parameterizing the optical response to produce a one-dimensional representation of at least a portion of a spectral window of the optical response in a high dimensional vector space, wherein the chemical parameter is pH and the optical response comprises a surface enhanced Raman scattering (SERS) spectral response that is a function of pH over at least about 5 pH units and wherein the adsorbate comprises more than one pH sensitive functional group.

11. The method of claim 10 wherein the nanoparticle comprises a shell surrounding a core material with a lower conductivity than the shell material, and selecting the thickness of the core material and the thickness of the shell material to generate a plasmon resonance frequency.

12. The method of claim 10 wherein parameterizing the SERB spectral response employs a local linear manifold approximation.

13. The method of claim 12 further comprising forcing the local linear manifold approximation to fit the one dimensional representation of the SERS spectral response to at least one linear segment.

14. A method comprising:
introducing an adsorbate associated with a nanoparticle to an environment of having an unknown chemical parameter, wherein the adsorbate comprises an optical response that is a function of the chemical parameter and wherein the adsorbate comprises more than one pH sensitive functional group;
acquiring the optical response of the adsorbate associated with a nanoparticle in the unknown environment; and
determining the chemical parameter of the unknown environment based on a comparison of the optical response of the adsorbate in a known environment to the optical response of the adsorbate in the unknown environment Wherein the chemical parameter is pH and the optical response comprises a surface enhanced Raman scattering (SERS) spectral response that is a function of pH over at least about 5 pH units.

15. The method of claim 14 wherein the SERS spectral response of the adsorbate is acquired by exciting the adsorbate and nanoparticle in vivo and/or in vitro.

16. The method of claim 14 wherein the unknown environment comprises a living tissue or cell.

17. The method of claim 16 wherein the living tissue or cell is experiencing a dysfunction or disorder.

18. The method of claim 17 farther comprising utilizing the adsorbate associated with the nanoparticle as a diagnostic tool.

19. A composition comprising a nanoparticle and at least one adsorbate associated with the nanoparticle, wherein the adsorbate displays a chemically responsive surface enhanced Raman scattering (SERS) spectral response that is a function of pH over at least 5 units, wherein the composition is operable as a pH sensor and wherein the optical sensor a pH resolution of about 0.1 pH units.

20. The composition of claim 1 wherein the adsorbate covers greater than about 5% of the surface area of the nanoparticle.

21. The method of claim 8 wherein the SERS response occurs over a pH range of from about 0 to about 14.

22. The method of claim 10 wherein the SERS response occurs over a pH range of from about 0 to about 14.

* * * * *

UNITED STATES PATENT AND TRADEMARK OFFICE
CERTIFICATE OF CORRECTION

| | |
|---|---|
| PATENT NO. | : 8,045,152 B2 |
| APPLICATION NO. | : 11/762430 |
| DATED | : October 25, 2011 |
| INVENTOR(S) | : Nancy J. Halas et al. |

It is certified that error appears in the above-identified patent and that said Letters Patent is hereby corrected as shown below:

Claim 2, column 13, line 8, between "claim" and "wherein" add "1"

Claim 3, column 13, line 16, replace "atmospheres" with --nanospheres--

Claim 12, column 14, line 10, replace "SERB" with --SERS--

Claim 14, column 14, line 29, replace "Wherein" with --wherein--

Claim 18, column 14, line 40, replace "farther" with --further--

Claim 19, column 14, line 48, between "sensor" and "a" add "has"

Signed and Sealed this
First Day of May, 2012

David J. Kappos
*Director of the United States Patent and Trademark Office*